(12) United States Patent
Haddadin

(10) Patent No.: US 11,135,715 B2
(45) Date of Patent: Oct. 5, 2021

(54) ROBOT ARM

(71) Applicant: Kastanienbaum GmbH, Munich (DE)

(72) Inventor: Sami Haddadin, Hannover (DE)

(73) Assignee: KASTANIENBAUM GMBH ( * ) Notice: Subject to any disclaimer, the term of this patent is extended or adjusted under 35 U.S.C. 154(b) by 6 days.

(21) Appl. No.: 15/766,942

(22) PCT Filed: Oct. 4, 2016

(86) PCT No.: PCT/EP2016/073621
§ 371 (c)(1),
(2) Date: Apr. 9, 2018

(87) PCT Pub. No.: WO2017/060212
PCT Pub. Date: Apr. 13, 2017

(65) Prior Publication Data
US 2018/0297192 A1 Oct. 18, 2018

(30) Foreign Application Priority Data
Oct. 8, 2015 (DE) .............. 10 2015 117 213.5

(51) Int. Cl.
G01L 5/00 (2006.01)
B25J 9/00 (2006.01)
G05B 19/423 (2006.01)
B25J 9/16 (2006.01)
B25J 13/08 (2006.01)
G06F 15/00 (2006.01)
C12Q 1/6886 (2018.01)

(52) U.S. Cl.
CPC .......... *B25J 9/0081* (2013.01); *B25J 9/1633* (2013.01); *B25J 13/085* (2013.01); *G05B 19/423* (2013.01); *C12Q 1/6886* (2013.01); *C12Q 2531/113* (2013.01)

(58) Field of Classification Search
CPC ...... B25J 9/0081; B25J 9/1633; B25J 13/085; G05B 19/423
USPC ........................................ 318/568.11; 702/41
See application file for complete search history.

(56) References Cited

U.S. PATENT DOCUMENTS

| 6,285,920 B1 | 9/2001 | McGee et al. | |
|---|---|---|---|
| 2009/0259412 A1* | 10/2009 | Brogardh | B25J 9/1633 702/41 |

FOREIGN PATENT DOCUMENTS

| CN | 101390027 A | 3/2009 |
|---|---|---|
| DE | 2841284 C2 | 4/1982 |
| DE | 3240251 A1 | 5/1984 |
| DE | 102013019869 A1 | 5/2015 |
| DE | 102013222456 A1 | 5/2015 |
| DE | 102014204452 A1 | 9/2015 |

(Continued)

OTHER PUBLICATIONS

Lumineau, Stéphane; PCT/EP2016/073621; International Search Report; ISA/EPO; dated Jan. 4, 2017.

(Continued)

*Primary Examiner* — Kawing Chan
*Assistant Examiner* — Zemenay T Truneh
(74) *Attorney, Agent, or Firm* — Todd Allen Serbin; Nexsen Pruet, LLC

(57) ABSTRACT

A robot arm permitting a more sensitive and precise operation in the offline programming of a robot having a robot arm with a number of arm components, which can be connected to a robot body via a number of actuator-drivable joint connections.

17 Claims, 2 Drawing Sheets

(56) References Cited

FOREIGN PATENT DOCUMENTS

| | | |
|---|---|---|
| DE | 102014216514 B3 | 9/2015 |
| EP | 0108348 A2 | 5/1984 |
| JP | S58160666 U | 10/1983 |
| JP | 59116806 A | 7/1984 |

OTHER PUBLICATIONS

Kraus, Thomas; DE Examination Report; DE 10 2015 117 213.5; dated Jun. 24, 2016.
Masahiro Takeichi, English Translation of First Examination report issued in parallel Japanese case, Application No. 2018-514268, dated May 21, 2019, 4 pages May 21, 2019.

\* cited by examiner

ROBOT ARM

RELATED APPLICATIONS

This application is a U.S. national phase application, claiming priority under 35 U.S.C. 371 to PCT application PCT/EP2016/073621, filed on Oct. 4, 2016, claiming priority to German national application 10 2015 117 213.5, filed on Oct. 8, 2015, the contents of the these applications incorporated by reference as if fully set forth herein in their entireties.

FIELD AND BACKGROUND OF THE INVENTION

The present invention relates to the robotics industry.

DETAILED DESCRIPTION OF THE INVENTION

Figure 1:
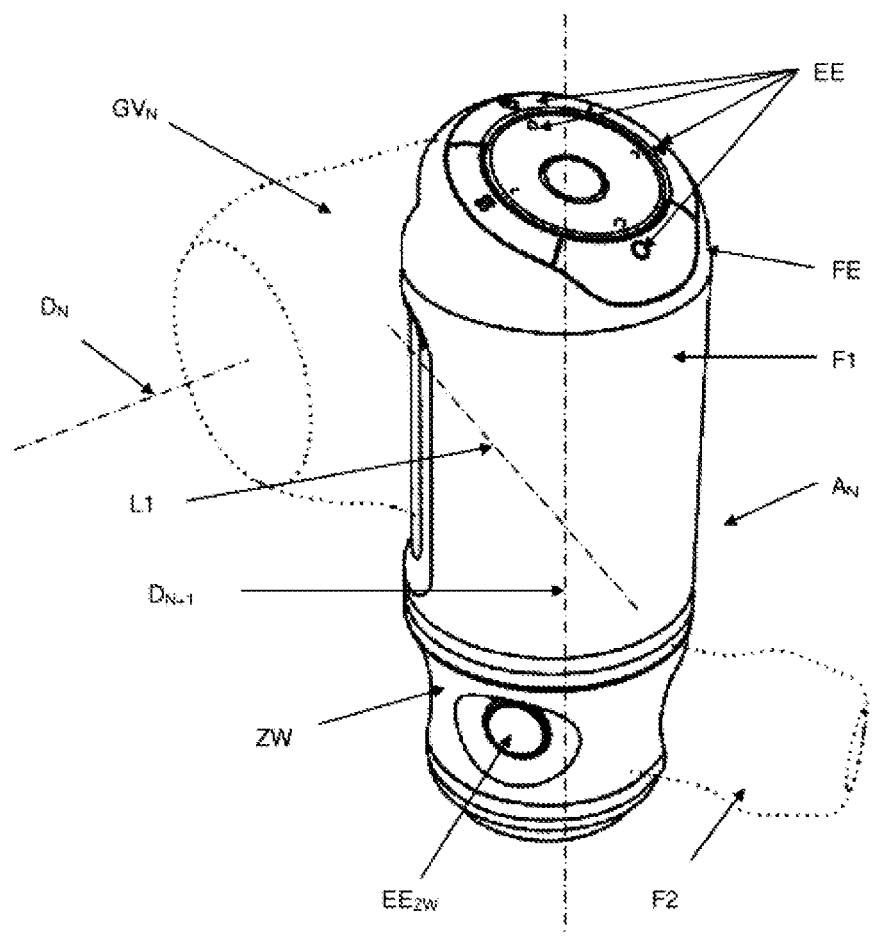
FIG. 1 shows a schematic partial view of an exemplary embodiment of the proposed robot arm; and,
FIG. 2 shows a schematic view of an exemplary embodiment of the proposed robot arm.
Figure 2:
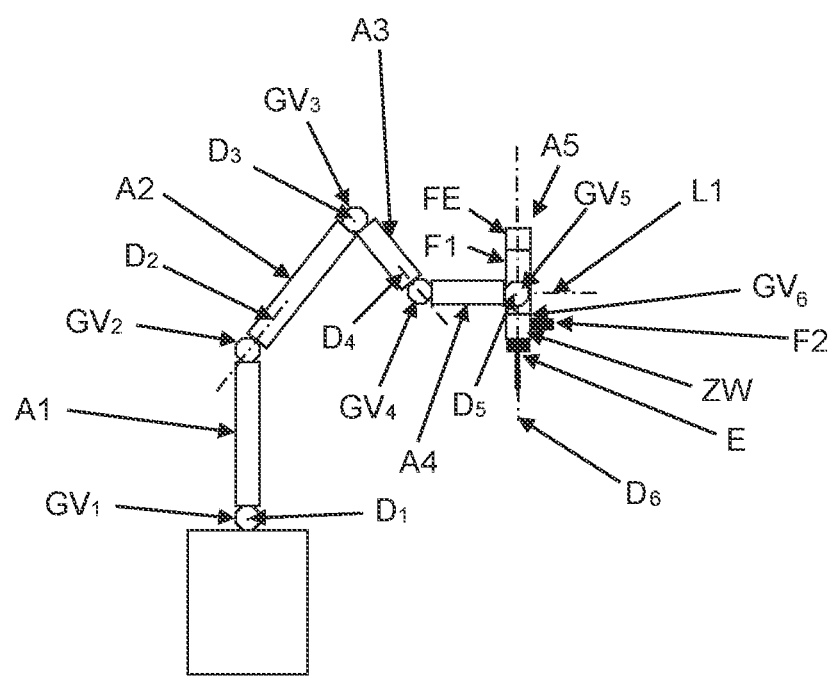

The invention relates to a robot arm with a number N of arm components $A_n$, which can be connected to a robot body via a number N of actuator-drivable joint connections $GV_n$. The invention also relates to a robot having a robot arm of this type.

So-called offline programming ("offline" process) of the robot is common in the interaction between human and robot. Here, a human being grips a robot arm of the robot, in particular at the final actuator, and carries out a movement of the robot arm to be taught. In doing so, the robot advantageously compensates for the inertia and the inherent weight of the robot arm. The movement executed by the robot arm is stored and can subsequently be carried out automatically by the robot. This enables simple and rapid programming of the robot. A reworking or optimization of the executed and stored movement of the robot arm is of course possible.

With this "offline" process, the robot arm must be gripped and guided from different positions. Furthermore, control elements and possibly indicator elements on the robot or on the robot arm are required in order to control offline programming and to enable status indications or other outputs.

The object of the invention is to specify a robot arm which enables improved offline programming of a robot having a robot arm.

The invention can be seen from the characteristics of the independent claims. Advantageous improvements and embodiments of the invention are the subject matter of the dependent claims. Further characteristics, possible applications and advantages of the invention can be seen from the following description and the explanation of exemplary embodiments of the invention, which are shown in the figures.

A first aspect of the invention relates to a robot arm, which has a number N of arm components $A_n$, which can be connected to a robot body via a number N of actuator-drivable joint connections $GV_n$ where n=1, 2, . . . , N.

According to the invention, the proposed robot arm is characterized in that the distal arm component $A_N$ of the robot arm is connected at its proximal end to the arm component $A_{N-1}$ via the joint connection $GV_N$, the proximal arm component $A_1$ of the robot arm can be connected at its proximal end to the robot body via the joint connection $GV_1$, the joint connection $GV_N$ permits a rotation of the arm component $A_N$ about a rotational axis $D_N$, the arm component $A_N$ of the robot arm extends along an axis L1 and the axis L1 encloses an angle of 50° to 130° with the rotational axis $D_N$, the distal end of the arm component $A_N$ can be connected to an actuator E via an actuator-drivable joint connection $GV_{N+1}$, wherein the joint connection $GV_{N+1}$ permits a rotation of the actuator E about a rotational axis $D_{N+1}$. Furthermore, according to the invention, the rotational axes $D_N$ and $D_{N+1}$ enclose an angle W1 in the range from 50° to 130°, and the rotational axis $D_{N+1}$ and the axis L1 enclose an angle W2 in the range from 50° to 130°, wherein a protrusion F2 is formed on the actuator E or on an intermediate part ZW arranged between the joint connection $GV_{N+1}$ and the actuator E, which protrusion extends perpendicular to the rotational axis $D_{N+1}$, can be gripped by a hand and is rigidly connected thereto (to the actuator E or to the joint connection $GV_{N+1}$ or to the arm component $A_N$).

In particular, the proposed robot arm enables a meticulous, sensitive and more accurate guidance and movement of the robot arm by an operator and therefore more accurate offline programming of a robot having a robot arm of this type. In particular, forces and moments can be specified more meticulously and more accurately during offline programming by means of the protrusion F2.

An advantageous development is characterized in that one or more input elements $EE_{ZW}$ are arranged on the intermediate part ZW within reach of a thumb of the hand gripping the protrusion F2. The input elements $EE_{ZW}$ are preferably arranged in such a way that a comfortable and ergonomic operation of the input elements $EE_{ZW}$ is possible.

An advantageous development is characterized in that the arm component $A_N$ has a grip-like protrusion F1 rigidly connected thereto (to the arm component $A_N$) which protrusion extends concentrically with respect to the rotational axis $D_{N+1}$, a free end FE of the protrusion can be rotated with respect to the rest of the protrusion F1 about the rotational axis $D_{N+1}$ or can be arranged rotatably about the rotational axis $D_{N+1}$, and the free end FE has input elements EE for the manual input of data.

The proposed arrangement and design of the input elements EE on the free end FE of the protrusion in particular enables good ergonomic operation, particularly during teach-programming, of a robot having such a robot arm. The input of information via the input elements EE is advantageously carried out manually, i.e. by means of touching or manual operation of the input elements EE.

Advantageously, the input elements EE are arranged on the free end FE at least partially concentrically with respect to the rotational axis $D_{N+1}$. That is to say that two, three, . . . or all the input elements EE are arranged concentrically with respect to the rotational axis $D_{N+1}$, advantageously with an identical radius to the rotational axis $D_{N+1}$. If the protrusion F1 is gripped by a hand and if the input elements EE are operated with the thumb of the hand, then the input elements EE are consistently well accessible or operable by the thumb, even with different alignments of the hand.

Advantageously, an input element $EE_0$ of the input elements EE is arranged axially with respect to the rotational axis $D_{N+1}$. Advantageously, this central input element $EE_0$ serves to input or control current primary parameters, for example to input a start time and a finish time for teach-programming Advantageously, the parameters input or controlled by means of the input elements EE and $EE_{ZW}$ respectively can be variably assigned or selected automatically or manually depending on the particular task.

Advantageously, the protrusion F1 and/or the protrusion F2 is designed such that it can be gripped by a hand of an operator, wherein a thumb of the hand comes to rest on the free end FE for operating the input elements EE or on the input elements $EE_{ZW}$. Advantageously, the protrusion F1 or the protrusion F2 has a cylindrical shape or an ergonomic grip shape for this purpose.

Advantageously, the free end FE of the protrusion F1 is ergonomically formed to operate the input elements EE with the thumb of the hand. For this purpose, in an embodiment, the input elements EE are arranged on a surface which is inclined at an angle of 5 to 60° with respect to a surface perpendicular to the rotational axis $D_{N+1}$. This inclination enables the input elements EE to be operated ergonomically, wherein, in particular, the distal thumb joint of the operating hand does not have to be bent, for example, at 90°.

Advantageously, the input elements EE and/or the input elements $EE_{ZW}$ have light elements with one or more controllable light sources. Advantageously, the light source/s are light emitting diodes LEDs.

Advantageously, the input elements EE and $EE_{ZW}$ are designed as buttons and/or rocker switches and/or pushbuttons and/or switches and/or rotary knobs and/or slide controllers. In a further advantageous embodiment, the input elements EE are designed as input fields of a touchpad (touch-sensitive surface) or a touchscreen (touch-sensitive display).

In a development of the proposed robot arm, the free end FE of the protrusion F1 can be detachably securely connected (for example, by means of latching or clip connections) to the rest of the protrusion F1 in different alignments about the rotational axis $D_{N+1}$. That is to say that the free end FE can be detached from the rest of the protrusion F1, which is rigidly connected to the robot arm, and can be used again with the rest of the protrusion F1 in a different position rotated with respect to the rotational axis $D_{N+1}$. This enables the input elements EE to be in each case optimally oriented with regard to their alignment relative to the hand gripping the protrusion F1. However, this alignment requires the free end FE to be detached every time and the free end FE reconnected to the rest of the protrusion F1 in a new angular orientation.

In a particularly advantageous embodiment of the robot arm, the free end FE of the protrusion F1 is securely connected rotatably about the rotational axis $D_{N+1}$ to the rest of the protrusion. In this embodiment, advantageously, the free end FE can be rotated freely (i.e. without a stop) about the rotational axis $D_{N+1}$. The detachment and reconnection of the free end FE, as described in the above development, is not required in this embodiment.

A development is characterized in that a mechanical and/or electrical and/or a magnetic latching device, which allows a rotation of the free end FE about the rotational axis $D_{N+1}$ with a specified resolution, is provided between the free end FE and the rest of the protrusion F1. In particular, this prevents unwanted rotation of the free end FE with respect to the rest of the protrusion F1. In order to move from one latching position to an adjacent latching position, it is necessary to apply a specified force or a specified torque to the free end FE. Advantageously, this force or this torque is chosen such that an ergonomic operation of the input elements is possible with different grip alignments of the hand on the protrusion F1. Advantageously, this force or this torque can be specified variably as required.

A development is characterized in that an output unit for outputting graphical and/or alphanumeric information is arranged on the arm component $A_N$. This enables the display or output of relevant information, for example while offline programming is being carried out.

A development is characterized in that the robot arm or, in particular the arm component $A_N$, has an interface via which a smartphone can be connected as an output unit. This interface can be a mechanical/electrical interface or a wireless interface (for example Bluetooth, WLAN etc.).

Advantageously, the protrusion F1 and the protrusion F2 are each gripped or guided by a hand of an operator.

In a particularly preferred embodiment, W1=90° and/or W2=90° are chosen for the angles mentioned in the introduction.

A further aspect of the invention relates to a robot having a robot arm as described above.

Advantageously, the robot comprises sensors for detecting a mechanical state Z(t) of the robot arm, a unit for detecting inputs EG(t) via the input elements EE and/or $EE_{ZW}$, a unit for evaluating the states Z(t) and the inputs EG(t) to determine evaluation results AW(t), and a storage unit for storing the evaluation results AW(t).

Advantageously, the evaluation results AW(t) are control instructions for controlling the robot arm. The proposed robot therefore enables the detection of states Z(t) of the robot arm which, in particular, are generated by the mechanical guidance of an operator, the detection of operator inputs via the input elements EE and/or $EE_{ZW}$, the evaluation of the detected states Z(t) and inputs and their conversion into evaluation results AW(t) which, in particular, constitute control instructions for carrying out the entered movements of the robot arm.

Here, advantageously, the mechanical state Z(t) is understood to mean the positioning of the robot arm, derivative/s with respect to time of the positioning of the robot arm, and/or forces and moments occurring and acting on the robot arm. The state Z(t) can, of course, include further time-dependent state parameters depending on the task and requirement. Advantageously, the unit for detecting the inputs includes the input elements EE and/or $EE_{ZW}$ as well as a processing unit PE1 connected to the input elements. Advantageously, the unit for evaluating the states Z(t) is a computer or a processing unit PE2, by means of which the appropriate evaluation program is executed. Advantageously, the processor units PE1 and PE2 are identical.

Further advantages, characteristics and details can be seen from the following description, in which at least one exemplary embodiment is described in detail—where appropriate with reference to the drawing.

FIG. 1 shows a schematic view of an exemplary embodiment of the proposed robot arm. The robot arm, shown in parts, has a number N of arm components $A_n$, which can be connected to a robot body via a number N of actuator-drivable joint connections GVn where n=1, 2, . . . , N. Only the arm component $A_{N-1}$ and $A_N$ is shown in FIG. 1. The robot arm shown in parts is characterized in that the distal arm component $A_N$ of the robot arm is connected at its proximal end to the arm component $A_{N-1}$ via the joint connection $GV_N$, the proximal arm component $A_1$ can be connected at its proximal end to the robot body (not shown) via the joint connection $GV_1$, the joint connection $GV_N$ permits a rotation of the arm component $A_N$ about a rotational axis $D_N$, the arm component $A_N$ of the robot arm extends along an axis L1 and the axis L1 encloses an angle of 90° with the rotational axis $D_N$, the distal end of the arm component $A_N$ can be connected to an actuator E (not shown) via an actuator-drivable joint connection $GV_{N+1}$, wherein the joint connection $GV_{N+1}$ permits a rotation of the actuator E about a rotational axis $D_{N+1}$, wherein the rotational axes $D_N$ and $D_{N+1}$ enclose an angle W1 in the region of 90°, and wherein the rotational axis $D_{N+1}$ and the axis L1 enclose an angle W2 of 90°.

The robot arm shown in parts is further characterized in that a protrusion F2 is formed on an intermediate part ZW arranged between the joint connection $GV_{N+1}$ and the actuator E (not shown), which protrusion extends perpendicular to the rotational axis $D_{N+1}$, i.e. extends radially, can be gripped by a hand and is rigidly connected thereto. Further, the arm component $A_N$ has a grip-like protrusion F1 rigidly connected to the arm component $A_N$ which protrusion extends concentrically with respect to the rotational axis $D_{N+1}$, wherein a free end FE of the protrusion F1 can be freely rotated about the rotational axis $D_{N+1}$ with respect to the rest of the protrusion F1, and the free end FE has input elements EE for the manual input of data.

Four axially arranged input elements EE, a central axially arranged input element EE and, on quenched surfaces, a total of four further input elements EE are arranged on the top of the free rotatable end FE. The electrical transmission of signals of the input elements EE between the detachable end FE and the rest of the protrusion F1 is advantageously carried out by wires, or by means of a slip ring transmission, or by means of wireless transmission.

Advantageously, the input elements EE at least partially comprise light elements, by means of which, for example, a current input status can be output and/or which serve to identify currently active input elements EE, and/or serve simply to illuminate the input elements EE. Furthermore, advantageously, the robot arm has an audible and/or visual output unit, by means of which a status generated in conjunction with an operation of an input element EE can be output audibly and/or visually. This enables a robot status or alarms to be output via the output unit.

The flexible arrangement of the detachable free end FE enables a suitable alignment for the operator to enable inputs to be made from different perspectives and gripping directions.

In particular, the protrusion F2 enables sensitive and accurate positioning and specification of forces or moments during the so-called "offline" process. Advantageously, the "offline" process takes place in that a hand of an operator grips the protrusion F1 and the other hand the protrusion F2, and required inputs to the input elements EE and $EE_{ZW}$ are made by means of the respective thumbs.

Although the invention has been illustrated and described in detail by means of preferred embodiments, the invention is not restricted to the disclosed examples, and other variations can be derived therefrom by the person skilled in the art without departing from the scope of protection of the invention. It is therefore clear that a multiplicity of possible variations exists. It is likewise clear that embodiments cited by way of example do indeed only constitute examples which are not to be regarded in any way as restricting the scope of protection, the possible applications or the configuration of the invention. Rather, the above description and the description of the figures enable the person skilled in the art to specifically implement the exemplary embodiments, wherein, with a knowledge of the disclosed inventive idea, the person skilled in the art can make various changes, for example with regard to the function or the arrangement of individual elements cited in an exemplary embodiment, without departing from the scope of protection which is defined by the claims and their legal equivalents, such as further explanations in the description.

The invention claimed is:

1. A robot arm comprising:
    a number N of arm components $A_n$, which can be connected to a robot body via a number N of actuator-driven joint connections $GV_n$, where n =1, 2, ..., N; wherein
        a distal arm component $A_N$ of the robot arm is connected at its proximal end to the arm component $A_{N-1}$ via the joint connection $GV_N$,
        a proximal arm component $A_1$ is connected at its proximal end to the robot body via the joint connection $GV_1$,
        the joint connection $GV_N$ permits a rotation of the arm component $A_N$ about a rotational axis $D_N$,
        the distal arm component $A_N$ of the robot arm extends transversely with respect to axis L1 and the axis L1 encloses an angle of 50° to 130° with the rotational axis $D_N$,
        a distal end of the arm component $A_N$ is connected to an actuator E via an actuator-driven joint connection $GV_{N+1}$, wherein the joint connection $GV_{N+1}$ permits a rotation of the actuator E about a rotational axis $D_{N+1}$, wherein
            the rotational axes $D_N$ and $D_{N+1}$ enclose an angle W1 in the range from 50° to 130°,
            the rotational axis $D_{N+1}$ and the axis L1 enclose an angle W2 in the range from 50° to 130°, and
        a protrusion F2 is formed on the actuator E or on an intermediate part ZW arranged between the joint connection $GV_{N+1}$ and the actuator E, which protrusion extends perpendicular to the rotational axis $D_{N+1}$, can be gripped by a hand and is rigidly connected thereto; and
    wherein the arm component $A_N$ has a grip-like protrusion F1 rigidly connected thereto which protrusion extends concentrically with respect to the rotational axis $D_{N+1}$, a free end FE of the protrusion F1 can be rotated with respect to the rest of the protrusion F1 about the rotational axis $D_{N+1}$ or can be arranged rotatably about the rotational axis $D_{N+1}$, and the free end FE has input elements EE for the manual input of data.

2. The robot arm according to claim 1, in which one or more input elements $EE_{ZW}$ are arranged on the intermediate part ZW within reach of a thumb of the hand.

3. The robot arm according to claim 1, in which the input elements EE are arranged on a surface which is inclined at an angle of 5 to 60° with respect to a surface perpendicular to the rotational axis $D_{N+1}$.

4. The robot arm according to claim 3, in which the free end FE can be detachably securely connected to the rest of the protrusion F1 in different alignments about the rotational axis $D_{N+1}$.

5. The robot arm according to claim 3, in which the free end FE is securely connected rotatably about the rotational axis $D_{N+1}$ to the rest of the protrusion F1.

6. The robot arm according to claim 3, in which a mechanical and/or electrical and/or a magnetic latching device, which allows a rotation of the free end FE about the rotational axis $D_{N+1}$ with a specified resolution, is provided between the free end FE and the rest of the protrusion F1.

7. The robot arm according to claim 1, in which the free end FE can be detachably securely connected to the rest of the protrusion F1 in different alignments about the rotational axis $D_{N+1}$.

8. The robot arm according to claim 7, in which the free end FE is securely connected rotatably about the rotational axis $D_{N+1}$ to the rest of the protrusion F1.

9. The robot arm according to claim 7, in which a mechanical and/or electrical and/or a magnetic latching device, which allows a rotation of the free end FE about the rotational axis $D_{N+1}$ with a specified resolution, is provided between the free end FE and the rest of the protrusion F1.

10. The robot arm according to claim 1, in which the free end FE is securely connected rotatably about the rotational axis $D_{N+1}$ to the rest of the protrusion F1.

11. The robot arm according to claim 10, in which a mechanical and/or electrical and/or a magnetic latching device, which allows a rotation of the free end FE about the rotational axis $D_{N+1}$ with a specified resolution, is provided between the free end FE and the rest of the protrusion F1.

12. The robot arm according to claim 1, in which a mechanical and/or electrical and/or a magnetic latching device, which allows a rotation of the free end FE about the rotational axis $D_{N+1}$ with a specified resolution, is provided between the free end FE and the rest of the protrusion F1.

13. A robot having a robot arm according to claim 1.

14. A robot having a robot arm according to claim 1, further comprising:
   sensors for detecting a mechanical state Z(t) of the robot arm,
   a unit for detecting inputs EG(t) via the input elements,
   a unit for evaluating the states Z(t) and the inputs EG(t) to determine evaluation results AW(t), and
   a storage unit for storing the evaluation results AW(t).

15. The robot according to claim 14, in which the evaluation results AW(t) are control instructions for controlling the robot arm robot.

16. A robot having a robot arm according to claim 1, in which evaluation results AW(t) are control instructions for controlling the robot arm robot.

17. The robot arm according to claim 1, in which the input elements EE are arranged on a surface which is inclined at an angle of 5 to 60° with respect to a surface perpendicular to the rotational axis $D_{N+1}$.

* * * * *